United States Patent [19]

Knapp et al.

[11] Patent Number: 5,037,744
[45] Date of Patent: *Aug. 6, 1991

[54] PROCESS FOR THE MICROBIOLOGICAL PREPARATION OF HUMAN SERUM ALBUMIN

[75] Inventors: Michael Knapp; Georges Bréfort; Paolo Sarmientos, all of Paris, France

[73] Assignee: Genetica, Joinville Le Pont, France

[*] Notice: The portion of the term of this patent subsequent to Apr. 3, 2007, has been disclaimed.

[21] Appl. No.: 449,351

[22] Filed: Dec. 13, 1989

Related U.S. Application Data

[63] Continuation of Ser. No. 843,602, Mar. 25, 1986, abandoned.

[30] Foreign Application Priority Data

Mar. 25, 1985 [FR] France ............................... 8504384

[51] Int. Cl.$^5$ ..................... C12P 21/02; C12N 15/70; C12N 15/14; C07K 13/00
[52] U.S. Cl. ................... 435/69.6; 435/69.8; 435/172.3; 435/172.1; 435/320.1; 530/350; 530/362; 530/364; 935/41; 935/29; 935/44; 935/45
[58] Field of Search ............... 435/172.1, 172.3, 320, 435/69.6, 71.1; 530/350, 362, 364

[56] References Cited

U.S. PATENT DOCUMENTS

| | | | |
|---|---|---|---|
| 4,511,502 | 4/1985 | Builder et al. | 260/112 R |
| 4,551,433 | 11/1985 | DeBoer | 435/253 |
| 4,578,355 | 3/1986 | Rosenberg | 435/317 |
| 4,792,523 | 12/1988 | Wong et al. | 435/68 |
| 4,831,120 | 5/1989 | Aviv et al. | 530/399 |
| 4,914,027 | 3/1990 | Knapp et al. | 435/69.6 |

FOREIGN PATENT DOCUMENTS

| | | |
|---|---|---|
| 0079739 | 5/1983 | European Pat. Off. |
| 0073646 | 9/1983 | European Pat. Off. |
| 0091527 | 10/1983 | European Pat. Off. |
| 0138437 | 4/1984 | European Pat. Off. |

OTHER PUBLICATIONS

Beaucage et al. (1981) Deoxy Nucleoside Phosphoramidites—A New Class of Key Intermediates for Deoxypolynucleotide Synthesis, Tetrahedron Letters, 22, 1859–1862.

Proceedings of the National Academy of Sciences of the USA, vol. 81, No. 3, Feb. 1984, pp. 669–673.

*Primary Examiner*—Elizabeth C. Weimar
*Assistant Examiner*—Christopher Low
*Attorney, Agent, or Firm*—Morgan & Finnegan

[57] ABSTRACT

Human serum albumin is made by culturing a bacterium (e.g. *E. coli*) capable of providing for the stable maintenance of a plasmid containing an inducible promoter (e.g. P$_{trp}$), a ribosome binding site (e.g. that of the CII gene of bacteriophage lambda not containing the t$_{R1}$ sequence), and the human serum albumin gene possessing an ATG initiation codon at the 5' end.

4 Claims, 25 Drawing Sheets

Fig. 3a pXL53 INSERTION SEQUENCE

```
        10        20        30        40        50        60        70        80
EcoRI
GAATTCCTCACTCATTAGGCACCCCCAGGCTTTTACACATTTATGCTTCCGGCTCGTATGTTGTGTGGAATTGTGAGCGG
CTTAAGGAGTGAGTAATCCGTGGGGGTCCGAAAAATGTGTAAATACGAAGGCCGAGCATACAACACACCTTAACACTCGCC 90       100       110       120       130       140       150       160
                             ①→
ATAACAATTTCACACAGGAAACAGGAATCCATGGATGCACACAAGAGTGAGGTTGCTCATCGGTTTAAAGATTTGGGAGA
TATTGTTAAAGTGTGTCCTTTGTCCTTAGGTACCTACGTGTGTTCTCACTCCAACGAGTAGCCAAATTTCTAAACCCTCT 170       180       190       200       210       220       230       240
AGAAAAATTTCAAAGCCCTTGGGTGTTGATTGCCTTTGCTCAGTATCTTCAGCAGTGTCCATTTGAAGATCATGTAAAATTAG
TCTTTTAAAGTTTCGGGAACCACAACTAAGGGAAACGAGTCATAGAAGTCGTCACAGGTAAACTTCTAGTACATTTAATC 250       260       270       280       290       300       310       320
TGAATGAAGTAACTGAATTTGCAAAAACATGTGTTGCTGATGAGTCAGCTGAAAATTGTGACAAATCACTTCATACCCTT
ACTTACTTCATTGACTTAAACGTTTTTGTACACAACGACTACTCAGTCGACTTTTAACACTGTTTAGTGAAGTATGGGAA
```

Fig. 3b

```
        330       340       350       360       370       380       390       400
TTTGGAGACAAATTATGCACAGTTGCAACTCTTCGTGAAACCTATGGTGAAATGGCTGACTGCTGTGCAAAACAAGAACC
AAACCTCTGTTAATACGTGTCAACGTTGAGAAGCACTTTGGATACCACTTACCGACTGACGACACGTTTGTTCTTGG 410       420       430       440       450       460       470       480
TGAGAGAAATGAATGCTTCTTGCAACACAAAGATGACAATCCAAATCTCCCCCGATTGGTGAGACCAGAGGTTGATGTGA
ACTCTCTTTACTTACGAAGAACGTTGTGTTTCTACTGTTAGGGTTTAGAGGGGGCTAACCACTCTGGTCTCCAACTACACT 490       500       510       520       530       540       550       560
TGTGCACTGCTTTTCATGACAATGAAGAGACATTTTGAAAAAATACTTATATGAATTGCCAGAAGACATCCTTACTTT
ACACGTGACGAAAAGTACTGTTACTTCTCTGTAAAAACTTTTTTATGAATATACTTAACGGTCTTCTGTAGGAATGAAA 570       580       590       600       610       620       630       640
TATGCCCCGGAACTCCTTTTCTTTGCTAAAAGGTATAAAGCTGCTTTTACAGAATGTTGCCAAGCTGCTGATAAAGCAGC
ATACGGGGCCTTGAGGAAAAGAAACGATTTTCCATATTTCGACGAAAATGTCTTACAACGGTTCGACGACTATTTCGTCG
```

Fig. 3c

```
         650        660        670        680        690        700        710        720
CTGCCTGTTGCCAAAGCTCGATGAACTTCGGGATGAAGGGAAGGCTTCGTCTGCCAAACAGAGACTCAAGTGTGCCAGTC
GACGGACAACGGGTTTCGAGCTACTTGAAGCCCTACTTCCCTTCCGAAGCAGACGGGTTTGTCTCTGAGTTCACACGGTCAG 730        740        750        760        770        780        790        800
TCCAAAAATTTGGGAGAAAGAGCTTTCAAAGCATGGGCAGTAGCTCGCCTGAGCCAGAGATTTCCCAAAGCTGAGTTTGCA
AGGTTTTAAACCCTCTTTCTCGAAAGTTTCGTACCCGTCATCGAGCGGACTCGGTCTCTAAAGGGTTTCGACTCAAACGT 810        820        830        840        850        860        870        880
GAAGTTTCCAAGTTAGTGACAGATCTTACCAAAGTCCACACGGAATGCTGCCATGGAGATCTGCTTGAATGTGCTGATGA
CTTCAAAGGTTCAATCACTGTCTAGAATGGTTTCAGGTGTGCCTTACGACGGTACCCTCTAGACGAACTTACACGACTACT 890        900        910        920        930        940        950        960
CAGGGCGGACCCTTGCCAAGTATATCTGTGAAAATCAAGATTCGATCTCCAGTAAACTGAAGGAATGCTGTGAAAAACCTC
GTCCCGCCTGGAACGGTTCATATAGACACTTTTAGTTCTAAGCTAGAGGTCATTTGACTTCCTTACGACACTTTTGGAG
```

Fig. 3d

```
       970       980       990      1000      1010      1020      1030      1040
TGTTGGAAAAATCCCACTGCATTGCCGAAGTGGAAAATGATGAGATGCCTGCTGACTTGCCTTCATTAGCGGCTGATTTT
ACAACCTTTTAGGGTGACGTAACGGCTTCACCTTTTACTACTCTACGGACGACTGAACGGAAGTAATCGCCGACTAAAA 1050      1060      1070      1080      1090      1100      1110      1120
GTTGAAAGTAAGGATGTTTGCAAAAACTATGCTGAGGCAAAGGATGTCTTCTTGGGCATGTTTTTGTATGAATATGCAAG
CAACTTTCATTCCTACAAACGTTTTGATACGACTCCGTTTCCTACAGAAGAACCCGTACAAAAACATACTTATACGTTC 1130      1140      1150      1160      1170      1180      1190      1200
AAGGCATCCTGATTACTCTGTCGTACTGCTGCTGAGACTTGCCAAGACATATGAAACCACTCTAGAGAAGTGCTGTGCCG
TTCCGTAGGACTAATGAGACAGCATGACGACGACTCTGAACGGTTCTGTATACTTTGGTGAGATCTCTTCACGACACGGC 1210      1220      1230      1240      1250      1260      1270      1280
CTGCAGATCCTCATGAATGCTATGCCAAAGTGTTCGATGAATTAAACCCTCTTATGGAAGAGCCTCAGAATTTAATCAAA
GACGTCTAGGAGTACTTACGATACGGTTTCACAAGCTACTTAAATTTGGAGAATACCTTCTCGGAGTCTTAAATTAGTTT
```

Fig. 3e

```
         1290       1300       1310       1320       1330       1340       1350       1360
    CAAAAATTGTGAGCTTTTGAGCAGCTTGGAGAGTACAAATTCCAGAATGCGCTATTAGTTCGTTACACCAAGAAAGTACC
    GTTTTAACACTCGAAAAACTCGTCGAACCTCTCTCATGTTTAAGGTCTTACGCGATAATCAAGCAATGTGGTTCTTTCATGG 1370       1380       1390       1400       1410       1420       1430       1440
    CCAAGTGTCAACTCCAACTCTTGTAGAGGTCTCAAGAAACCTAGGAAAAGTGGGCAGCAAATGTTGTAAACATCCTGAAG
    GGTTCACAGTTGAGGTTGAGAACATCTCCAGAGTTCTTTGGATCCTTTTCACCCGTCGTTTACAACATTTGTAGGACTTC 1450       1460       1470       1480       1490       1500       1510       1520
    CAAAAAGAATGCCCTGTGCAGAAGACTATCTATCCGTGGTCCTGAACCAGTTATGTGTTGCATGAGAAAACGCCAGTA
    GTTTTTCTTACGGGACACGTCTTCTGATAGATAGGCACCAGGACTTGGTCAATACACAACGTACTCTTTTGCGGTCAT 1530       1540       1550       1560       1570       1580       1590       1600
    AGTGACAGAGTCACCAAATGCTGCACAGAATCCTTGGTGAACAGGCGACCATGCTTTTCACCTCTGGAAGTCGATGAAAC
    TCACTGTCTCAGTGGTTTACGACGTGTCTTAGGAACCACTTGTCCGCTGGTACGAAAAGTCGAGACCTTCAGCTACTTTG
```

Fig. 3f

```
         1610      1620      1630      1640      1650      1660      1670      1680
ATACGGTTCCCAAAGAGTTTAATGCTGAAACATTCACCTTCCATGCAGATATATGCACACTTTCTGAGAAGGAGAGACAAA 1690      1700      1710      1720      1730      1740      1750      1760
TATGCAAGGGTTTCTCAAATTACGACTTTGTAAGTGGAAGGTACGTCTATATACGTGTGAAAGACTCTTCCTCTCTGTTT 1690      1700      1710      1720      1730      1740      1750      1760
TCAAGAAAACAAACTGCACTTGTTGAGCTTGTGAAACACAAGGCAACAAAGAGCAACTGAAAGCTGTTATGGAT 1770      1780      1790      1800      1810      1820      1830      1840
AGTTCTTTGTTTGACGTGAACAACTCGAACACTTTGTGTTCCGTTGTTTCTCGTTGACTTTCGACAATACCTA 1770      1780      1790      1800      1810      1820      1830      1840
GATTTCGCAGCTTTTGTAGAGAAGTGCTGCAAGGCTGACGATAAGGAAACCTGCTTTGCCGAGGAGGGTAAAAAACTTGT 585  1870      1880      1890      1900      1910      1920
CTAAAGGCGTCGAAAACATCTCTTCACGACGTTCCGACTGCTATTCCTTTGGACGAAACGGCTCCTCCTCCCATTTTTGAACA 1850      1860      1870      1880      1890      1900      1910      1920
TGCTGCAAGTCAAGCTGCCTTAGGCTTATAACATCACATTTAAAAGCATCTCAGCCTACCATGAGAATAAGAGAAAGAAA

ACGACGTTCAGTTCGACGGAATCCGAATATTGTAGTGTAAATTTTCGTAGAGTCGGGATGGTACTCTTATTCTCTTTCTTT
```

Fig. 3g

```
        1930      1940      1950      1960      1970      1980      1990      2000
ATGAAGATCAAAAGCTTATTCATTCTGTTTTTCTTTTTCGTTGGTGTAAAAGCCAACACCCTGTCTAAAAAACATAAATT 2010      2020      2030      2040      2050      2060      2070      2080
TACTTCTAGTTTTTCGAATAAGTAAGACAAAAGAAAAAGCAACCACATTTTCGGTTGTGGGACAGATTTTTGTATTTAA 2090      2100      2110      2120      2130      2140      2150      2160
TCTTTAATCATTTTAATCATTTGCCTCTTTTCTCTGTGCTTCAATTAATAAAAATGGAAAGAATCTAAAAAAACCCCC
       PstI
AGAAATTAGTAAAATTAGTAAAACGGAGAAAAGAGACACGGAAGTTAATTATTTTTACCTTTCTTAGATTTTTTGGGGG

2090
        PstI
CCCCCCCCCCCTGCAGCAATAGCAACAACGTTGCGCAAACTATTAACTGGCGAA
GGGGGGGGGGGACGTCGTTGTTGCAACGCGTTTGATAATTGACCGCTT
```

Fig. 4a

TRANSLATION OF THE HUMAN ALBUMIN GENE IN pXL53

```
                    125             140             155             170
         ATG  GAT  GCA  CAC  AAG  AGT  GAG  GTT  GCT  CAT  CGG  TTT  AAA  GAT  TTG  GGA  GAA  GAA  AAT  TTC
         MET  ASP  ALA  HIS  LYS  SER  GLU  VAL  ALA  HIS  ARG  PHE  LYS  ASP  LEU  GLY  GLU  GLU  ASN  PHE 185             200             215             230
         AAA  GCC  TTG  GTG  TTG  ATT  GCC  TTT  GCT  CAG  TAT  CTT  CAG  CAG  TGT  CCA  TTT  GAA  GAT  CAT
         LYS  ALA  LEU  VAL  LEU  ILE  ALA  PHE  ALA  GLN  TYR  LEU  GLN  GLN  CYS  PRO  PHE  GLU  ASP  HIS 245             260             275             290
         GTA  AAA  TTA  GTG  AAT  GAA  GTA  ACT  GAA  TTT  GCA  AAA  ACA  TGT  GTT  GCT  GAT  GAG  TCA  GCT
         VAL  LYS  LEU  VAL  ASN  GLU  VAL  THR  GLU  PHE  ALA  LYS  THR  CYS  VAL  ALA  ASP  GLU  SER  ALA 305             320             335             350
         GAA  AAT  TGT  GAC  AAA  TCA  CTT  CAT  ACC  CTT  TTT  GGA  GAC  AAA  TTA  TGC  ACA  GTT  GCA  ACT
         GLU  ASN  CYS  ASP  LYS  SER  LEU  HIS  THR  LEU  PHE  GLY  ASP  LYS  LEU  CYS  THR  VAL  ALA  THR
```

Fig. 4b

```
                    365                    380                    395                    410
CTT CGT GAA ACC TAT GGT GAA ATG GCT GAC TGC TGT GCA AAA CAA GAA CCT GAG AGA AAT
LEU ARG GLU THR TYR GLY GLU MET ALA ASP CYS CYS ALA LYS GLN GLU PRO GLU ARG ASN 425                    440                    455                    470
GAA TGC TTC TTG CAA CAC AAA GAT GAC AAT CCA AAT CTC CCC CGA TTG GTG AGA CCA GAG
GLU CYS PHE LEU GLN HIS LYS ASP ASP ASN PRO ASN LEU PRO ARG LEU VAL ARG PRO GLU 485                    500                    515                    530
GTT GAT GTG ATG TGC ACT GCT TTT CAT GAC AAT GAA GAG ACA TTT TTG AAA AAA TAC TTA
VAL ASP VAL MET CYS THR ALA PHE HIS ASP ASN GLU GLU THR PHE LEU LYS LYS TYR LEU 545                    560                    575                    590
TAT GAA ATT GCC AGA AGA CAT CCT TAC TTT TAT GCC CCG GAA CTC CTT TTC TTT GCT AAA
TYR GLU ILE ALA ARG ARG HIS PRO TYR PHE TYR ALA PRO GLU LEU LEU PHE PHE ALA LYS
```

Fig. 4c

```
                605                     620                    635                                650
AGG TAT AAA GCT GCT TTT ACA GAA TGT TGC CAA GCT GCT GAT AAA GCA GCC TGC CTG TTG
ARG TYR LYS ALA ALA PHE THR GLU CYS CYS GLN ALA ALA ASP LYS ALA ALA CYS LEU LEU 665                     680                     695                              710
CCA AAG CTC GAT GAA CTT CGG GAT GAA GGG AAG GCT TCG TCT GCC AAA CAG AGA CTC AAG
PRO LYS LEU ASP GLU LEU ARG ASP GLU GLY LYS ALA SER SER ALA LYS GLN ARG LEU LYS 725                     740                     755                              770
TGT GCC AGT CTC CAA AAA TTT GGA GAA AGA GCT TTC AAA GCA TGG GCA GTA GCT CGC CTG
CYS ALA SER LEU GLN LYS PHE GLY GLU ARG ALA PHE LYS ALA TRP ALA VAL ALA ARG LEU 785                     800                     815                              830
AGC CAG AGA TTT CCC AAA GCT GAG TTT GCA GAA GTT TCC AAG TTA GTG ACA GAT CTT ACC
SER GLN ARG PHE PRO LYS ALA GLU PHE ALA GLU VAL SER LYS LEU VAL THR ASP LEU THR
```

Fig. 4d

```
                845                 860                 875                 890
AAA GTC CAC ACG GAA TGC TGC CAT GGA GAT CTG CTT GAA TGT GCT GAT GAC AGG GCG GAC
LYS VAL HIS THR GLU CYS CYS HIS GLY ASP LEU LEU GLU CYS ALA ASP ASP ARG ALA ASP 905                 920                 935                 950
CTT GCC AAG TAT ATC TGT GAA AAT CAA GAT TCG ATC TCC AGT AAA CTG AAG GAA TGC TGT
LEU ALA LYS TYR ILE CYS GLU ASN GLN ASP SER ILE SER SER LYS LEU LYS GLU CYS CYS 965                 980                 995                 1010
GAA AAA CCT CTG TTG GAA AAA TCC CAC TGC ATT GCC GAA GTG GAA AAT GAT GAG ATG CCT
GLU LYS PRO LEU LEU GLU LYS SER HIS CYS ILE ALA GLU VAL GLU ASN ASP GLU MET PRO 1025                1040                1055                1070
GCT GAC TTG CCT TCA TTA GCG GCT GAT TTT GTT GAA AGT AAG GAT GTT TGC AAA AAC TAT
ALA ASP LEU PRO SER LEU ALA ALA ASP PHE VAL GLU SER LYS ASP VAL CYS LYS ASN TYR
```

Fig. 4e

```
                        1085                        1100                        1115                        1130
GCT GAG GCA AAG GAT GTC TTC TTG GGC ATG TTT TTG TAT GAA TAT GCA AGA AGG CAT CCT
ALA GLU ALA LYS ASP VAL PHE LEU GLY MET PHE LEU TYR GLU TYR ALA ARG ARG HIS PRO 1145                        1160                        1175                        1190
GAT TAC TCT GTC GTA CTG CTG AGA CTT GCC AAG ACA TAT GAA ACC ACT CTA GAG AAG
ASP TYR SER VAL VAL LEU LEU ARG LEU ALA LYS THR TYR GLU THR THR LEU GLU LYS 1205                        1220                        1235                        1250
TGC TGT GCC GCT GCA GAT CCT CAT GAA TGC TAT GCC AAA GTG TTC GAT GAA TTT AAA CCT
CYS CYS ALA ALA ALA ASP PRO HIS GLU CYS TYR ALA LYS VAL PHE ASP GLU PHE LYS PRO 1265                        1280                        1295                        1310
CTT ATG GAA GAG CCT CAG AAT TTA ATC AAA CAA AAT TGT GAG CTT TTT GAG CAG CTT GGA
LEU MET GLU GLU PRO GLN ASN LEU ILE LYS GLN ASN CYS GLU LEU PHE GLU GLN LEU GLY
```

Fig. 4f

```
                    1325                              1340                                  1355                              1370
GAG TAC AAA TTC CAG AAT GCG CTA TTA GTT CGT TAC ACC AAG AAA GTA CCC CAA GTG TCA
GLU TYR LYS PHE GLN ASN ALA LEU LEU VAL ARG TYR THR LYS LYS VAL PRO GLN VAL SER 1385                              1400                                  1415                              1430
ACT CCA ACT CTT GTA GAG GTC TCA AGA AAC CTA GGA AAA GTG GGC AGC AAA TGT TGT AAA
THR PRO THR LEU VAL GLU VAL SER ARG ASN LEU GLY LYS VAL GLY SER LYS CYS CYS LYS 1445                              1460                                  1475                              1490
CAT CCT GAA GCA AAA AGA ATG CCC TGT GCA GAA GAC TAT CTA TCC GTG GTC CTG AAC CAG
HIS PRO GLU ALA LYS ARG MET PRO CYS ALA GLU ASP TYR LEU SER VAL VAL LEU ASN GLN 1505                              1520                                  1535                              1550
TTA TGT GTG TTG CAT GAG AAA ACG CCA GTA AGT GAC AGA GTC ACC AAA TGC TGC ACA GAA
LEU CYS VAL LEU HIS GLU LYS THR PRO VAL SER ASP ARG VAL THR LYS CYS CYS THR GLU
```

Fig. 4g

```
          1565                  1580                  1595                     1610
TCC TTG GTG AAC AGG CGA CCA TGC TTT TCA GCT CTG GAA GTC GAT GAA ACA TAC GTT CCC
SER LEU VAL ASN ARG ARG PRO CYS PHE SER ALA LEU GLU VAL ASP GLU THR TYR VAL PRO 1625                  1640                  1655                     1670
AAA GAG TTT AAT GCT GAA ACA TTC ACC TTC CAT GCA GAT ATA TGC ACA CTT TCT GAG AAG
LYS GLU PHE ASN ALA GLU THR PHE THR PHE HIS ALA ASP ILE CYS THR LEU SER GLU LYS 1685                  1700                  1715                     1730
GAG AGA CAA ATC AAG AAA CAA ACT GCA CTT GTT GAG CTT GTG AAA CAC AAG CCC AAG GCA
GLU ARG GLN ILE LYS LYS GLN THR ALA LEU VAL GLU LEU VAL LYS HIS LYS PRO LYS ALA 1745                  1760                  1775                     1790
ACA AAA GAG CAA CTG AAA GCT GTT ATG GAT GAT TTC GCA GCT TTT GTA GAG AAG TGC TGC
THR LYS GLU GLN LEU LYS ALA VAL MET ASP ASP PHE ALA ALA PHE VAL GLU LYS CYS CYS
```

Fig. 4h

```
                     1805              1820              1835              1850
AAG GCT GAC GAT AAG GAA ACC TGC TTT GCC GAG GAG GGT AAA AAA CTT GTT GCT GCA AGT
LYS ALA ASP ASP LYS GLU THR CYS PHE ALA GLU GLU GLY LYS LYS LEU VAL ALA ALA SER 1865           1880
              (585-STOP)
CAA GCT GCC TTA GGC TTA TAA CAT CAC ATT
GLN ALA ALA LEU GLY LEU
```

THE MOLECULAR WEIGHT OF THIS PROTEIN IS 66550.0

*1 --- 0.5 microgrammes of natural HSA (SIGMA)

*2 --- 1 microgramme of natural HSA (SIGMA)

*3 --- insoluble proteins containing the recombinant HSA, corresponding to 100 microlitres of bacterial culture having an optical density of $4(A_{610})$

Fig. 7.

Comparison between authentic human serum albumin
and human serum albumin prepared by the
microbiological preparation process

A B

10% native polyacrylamide gel

A - human serum albumin (Sigma)

B - recombinant human serum albumin after
renaturation

PROCESS FOR THE MICROBIOLOGICAL PREPARATION OF HUMAN SERUM ALBUMIN

This application is a continuation of application Ser. No. 843,602, filed Mar. 25, 1986, now abandoned.

FIELD OF THE INVENTION

The present invention relates to a new process for protein synthesis.

More especially, the invention relates to a process which employs in vitro genetic manipulation techniques to obtain a concerted rearrangement of deoxyribonucleic acid sequences, by means of which the synthesis of human serum albumin by a bacterium may be induced.

BACKGROUND OF THE INVENTION

Human serum albumin is a protein consisting of 585 amino acids which does not contain associated glycoside residues and has a molecular weight of the order of 66,000 daltons.

Genetically, human serum albumin is encoded in man by two codominant autosomal allelic genes. The genes for human serum albumin are notoriously polymorphic, and at least twenty-four variants of serum albumin are known, differentiated by their electrophoretic behaviour (Shell and Blumberg, "The genetics of human serum albumin", in "Albumin Structure, Function and Uses", Rosenoer, Oratz and Rothschild eds., Pergamon Press, 1977).

Serum albumin is synthesized in the hepatocytes, and then excreted into the serum in which it constitutes the most abundant protein, with mean concentrations of the order of 4g/100 ml of serum. It performs a major physiological role in the maintenance of the osmotic pressure of the plasma, and thus contributes to the stability of the balance between the internal (cellular) environment and the external (circulating) environment, which balance provides, among other functions, for the maintenance of a level of cell hydration which is compatible with the normal physiological functioning of the body.

Human serum albumin also performs a role in the transport of "natural" hydrophobic molecules (steroids and bile salts, for example) and drug molecules to their sites of action.

This explains why human serum albumin is used both in the therapy of blood volume disorders, for example posthaemorrhagic acute hypovolaemia or extensive burns, and in supportive therapy in so-called volume expansion solutions in general surgery, and in the treatment of dehydration states (for example nephrotic syndromes), all these uses demanding the supply of considerable amounts of serum albumin (several tens of grammes per day per patient).

Human serum albumin is at present extracted from serum by techniques derived from that of E.J. Cohn et al., J. Am. Chem. Soc. (1946), 68, p. 459 et seq., or from placenta by the technique of J. Liautaud et al., 13th Internat. Congress of IABS, Budapest; A: Purification of Proteins, Development of Biological Standard (1973) Karger, ed., Bale, 27, p. 107 et seq. These sources, which hardly meet the requirements of the world market, suffer from several defects, inter alia their uncertain nature. Moreover, they are not devoid of the risk of contamination (hepatitis, for example, and more recently acquired immunodeficiency syndrome), and this would have dramatic consequences when the protein was used in therapy.

In vitro genetic recombination techniques now offer the possibility of making a micro-organism, for example the *Escherichia coli* bacterium, synthesize any protein or any polypeptide and, in theory, doing this in unlimited quantities (see for example F. Gros et al., Sciences de la Vie et Société, Documentation Francaise ed., 1979).

Since the classical experiments of F. Jacob et al., it is known that DNA contains, on the one hand a group of so-called "structural" genes, that is to say genes which code for a given protein, and on the other hand so-called "regulator" genes, that is to say genes capable of modulating the expression of the structural genes, the combination of the two types forming an entity known as an "operon".

Research in molecular biology and the development of DNA sequencing techniques [F. Sanger and A.R. Coulson, J. Mol. Biol. (1975), 94, p. 441 et seq., A.M. Maxam and W. Gilbert, Proc. Natl. Acad. Sci. (USA) (1977), 74, p. 560 et seq.] have made it possible to specify the organization of the operon as it had been conceived by F. Jacob and J. Monod [F. Jacob and J. Monod, Cold Spring Harbor Symp. Quant. Biol. (1961), 26, p. 193 et seq.; F. Jacob and J. Monod, J. Mol. Biol. (1961), 26 p. 318 et seq.], and to identify the special features of the primary structure of the two types of gene.

Thus, all structural genes are enclosed by a so-called "translation initiation" codon (ATG) and a "stop" codon. The function of the initiation codon is to bind a transfer RNA bearing a formylmethionine. The protein chain will elongate from this formylmethionine by successive attachment of amino acids encoded by the structural gene; the "stop" codon will finally cause the elongation to stop and bring about the release of the newly formed protein.

As regards the regulating genes (promoters, repressors), a promoter, for example, being defined as a DNA fragment to which RNA polymerase is bound, it has been possible to identify the most highly conserved sequences [D. Pribnow, Proc. Natl. Acad. Sci. (USA) (1975), 72, p. 784 et seq.]; similarly, it has been possible to define the most highly conserved DNA sequences at the level of the ribosome binding sites (RBS) [J. Shine and L. Dalgarno, Nature (1975), 254, p. 34 et seq.], which sites perform a role in the translation of the transcribed RNA to protein.

Thus, the bacterial regulator genes can hence be defined by their functional properties and also by their primary sequence, and in vitro genetic recombination techniques turn this to good account to place any structural gene under their control, this being possible as a result of the existence of "restriction enzymes" which cut the DNA at specific points [H.O. Smith and K.W. Wilcox, J. Mol. Biol. (1970), 51, p. 379 et seq., M. Meselson and R. Yuan, Nature (1968), 217, p. 1110 et seq., R.J. Roberts, Nucleic Acids Res. (1982), 1, p. 135 et seq.].

The techniques used, which are in other respects known, employ the concerted use of these enzymes to cut the DNA at predetermined points, and enzymes known as "ligases" to link the fragments together [P.E. Loban and A.D. Kaiser, J. Mol. Biol. (1973), 78, p. 453 et seq.] The assembly is carried by "vectors" (plasmids or bacteriophages) capable of being introduced into a bacterium such as *E. coli* by processes which are in other respects known, and of being maintained there during the growth of the host bacterium [M. Mandel and A. Higa, J. Mol. Biol. (1970), 53, p. 154 et seq.].

DETAILED DESCRIPTION OF THE INVENTION

Figure 1:
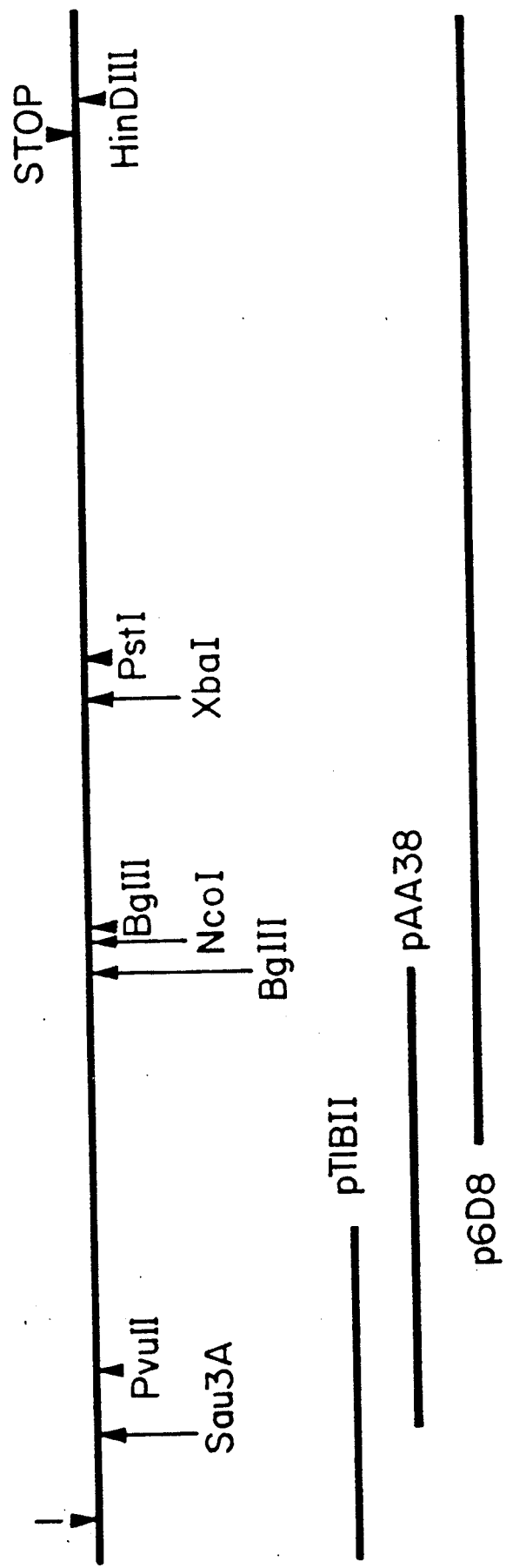
Figure 2A:
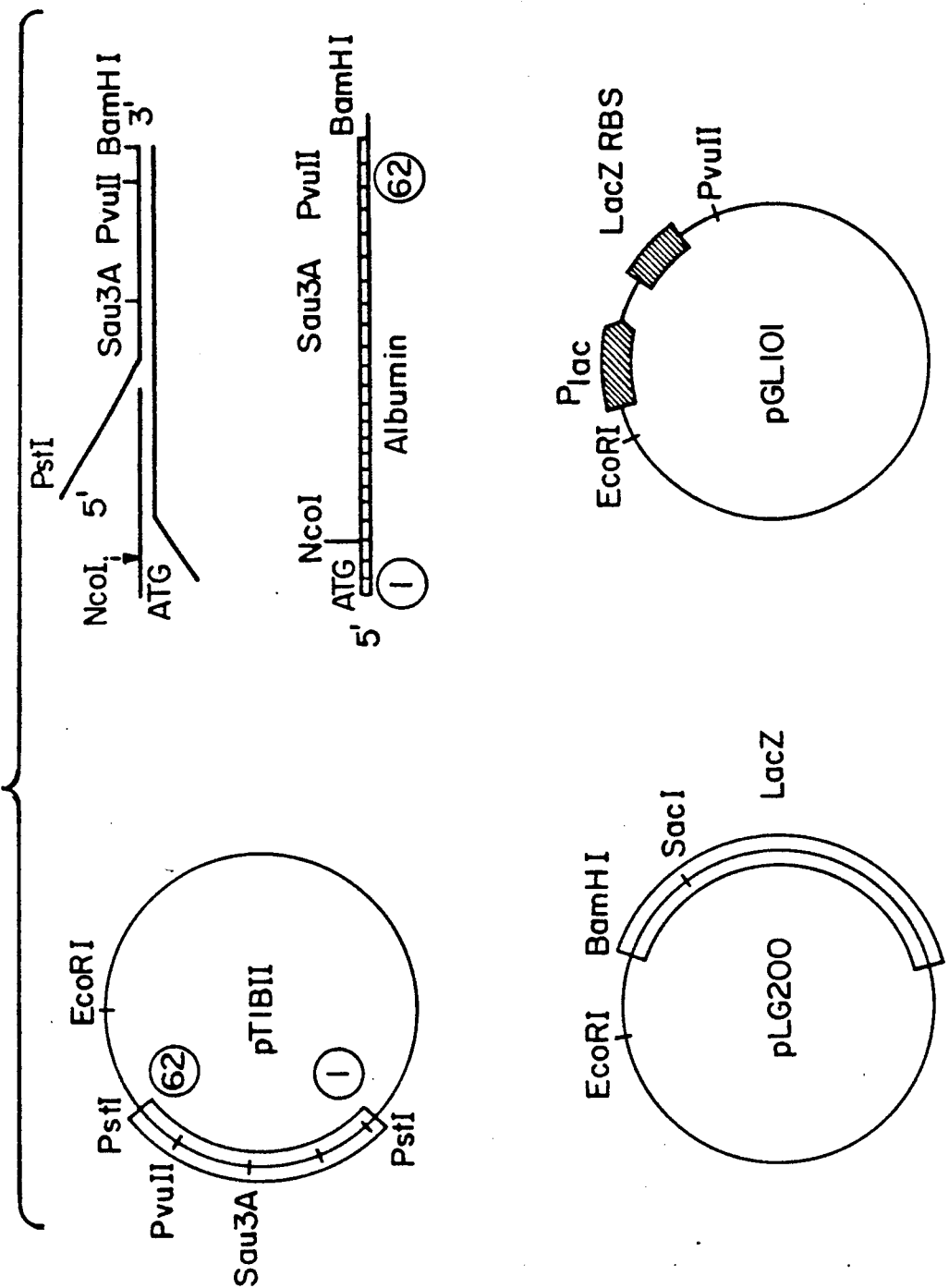
Figure 2B:
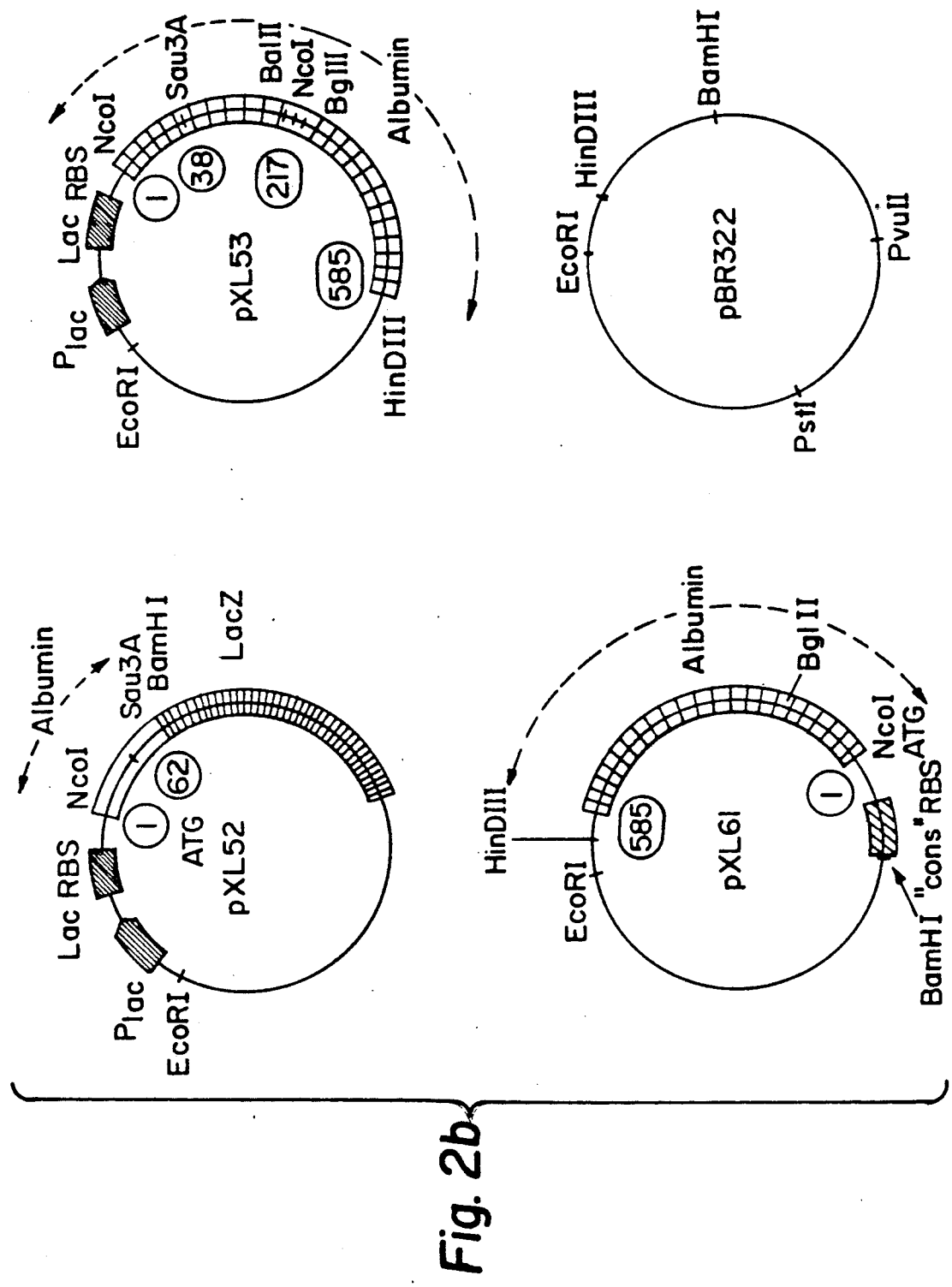
Figure 2C:
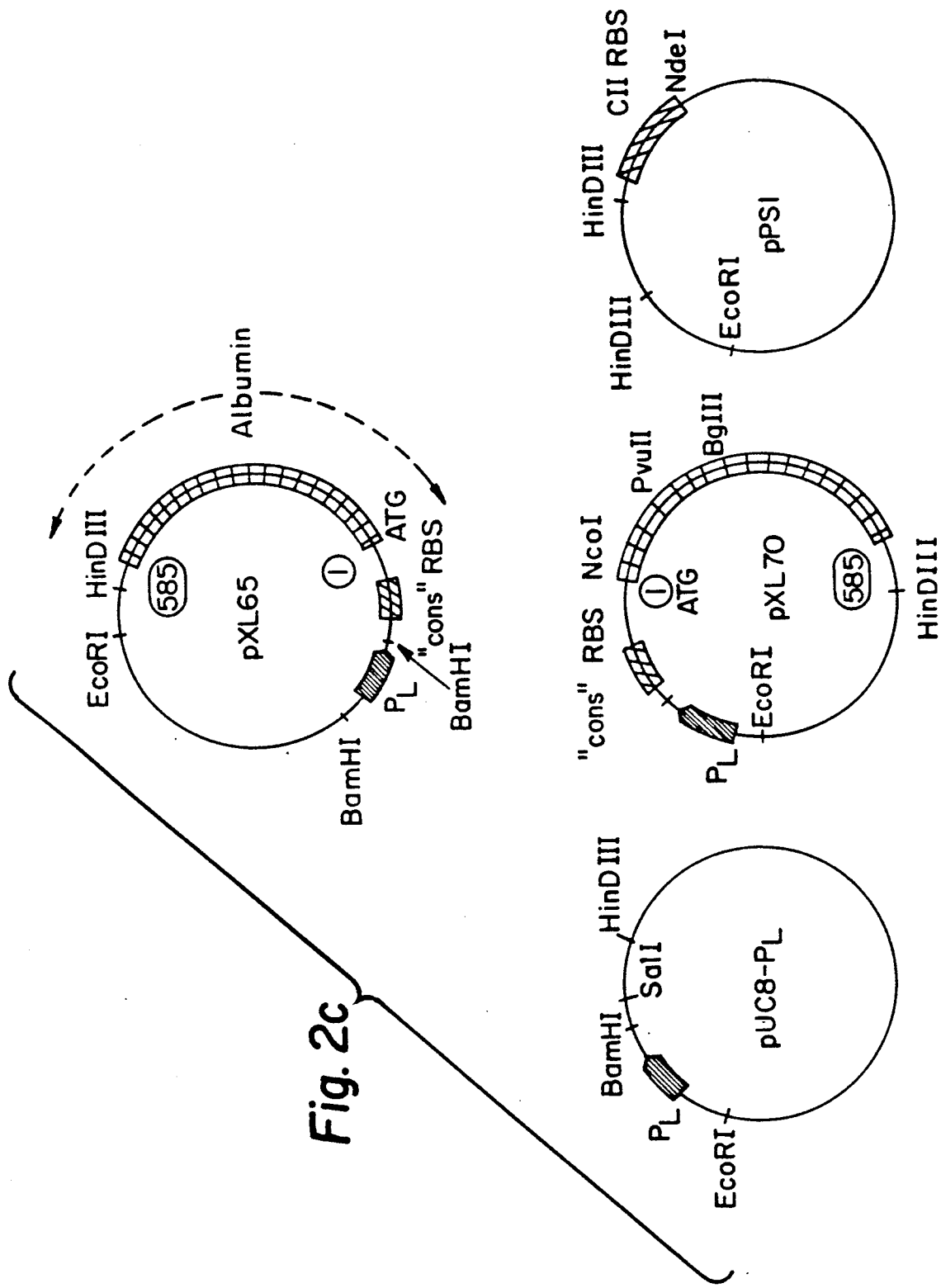
Figure 2D:
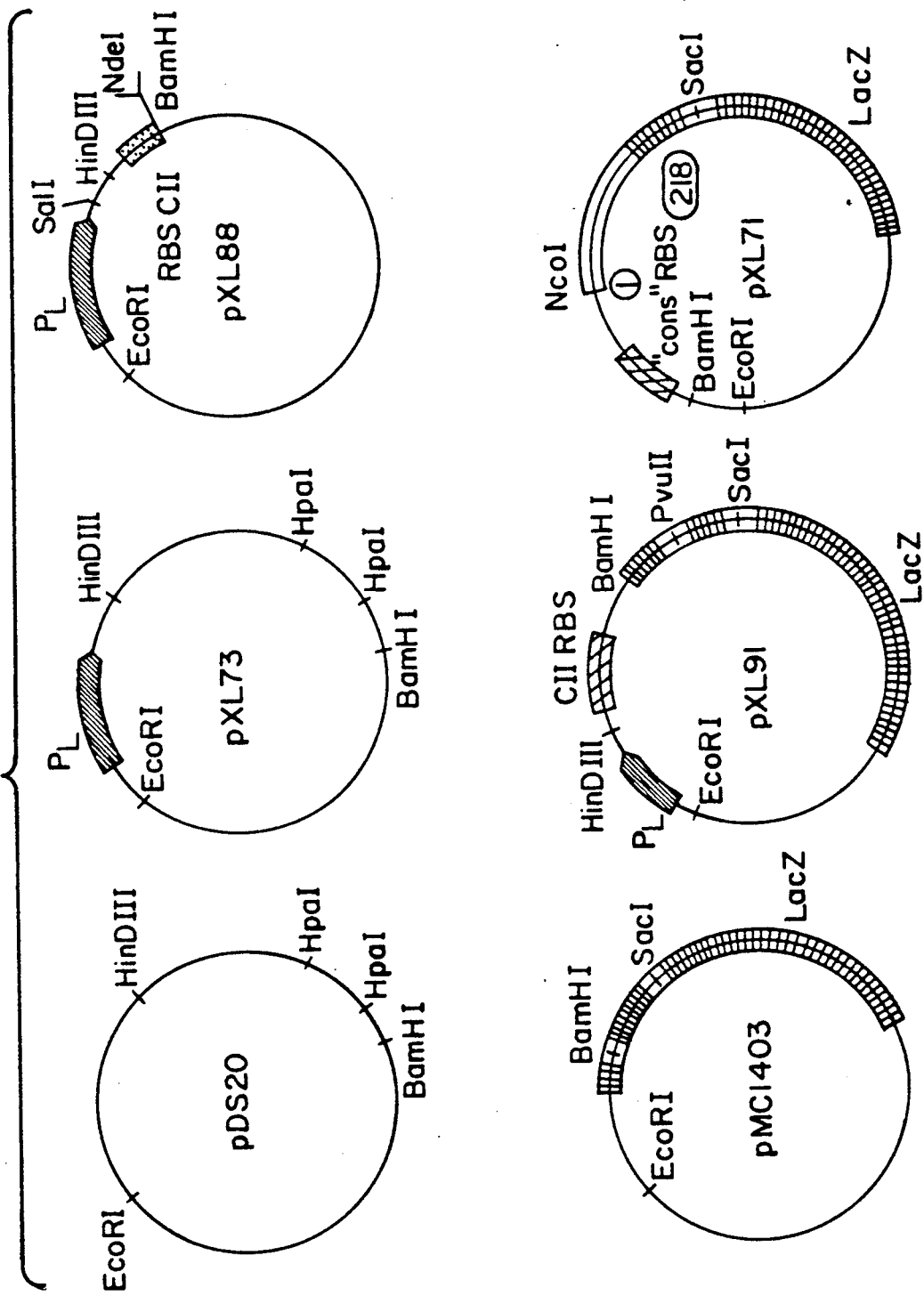
Figure 2E:
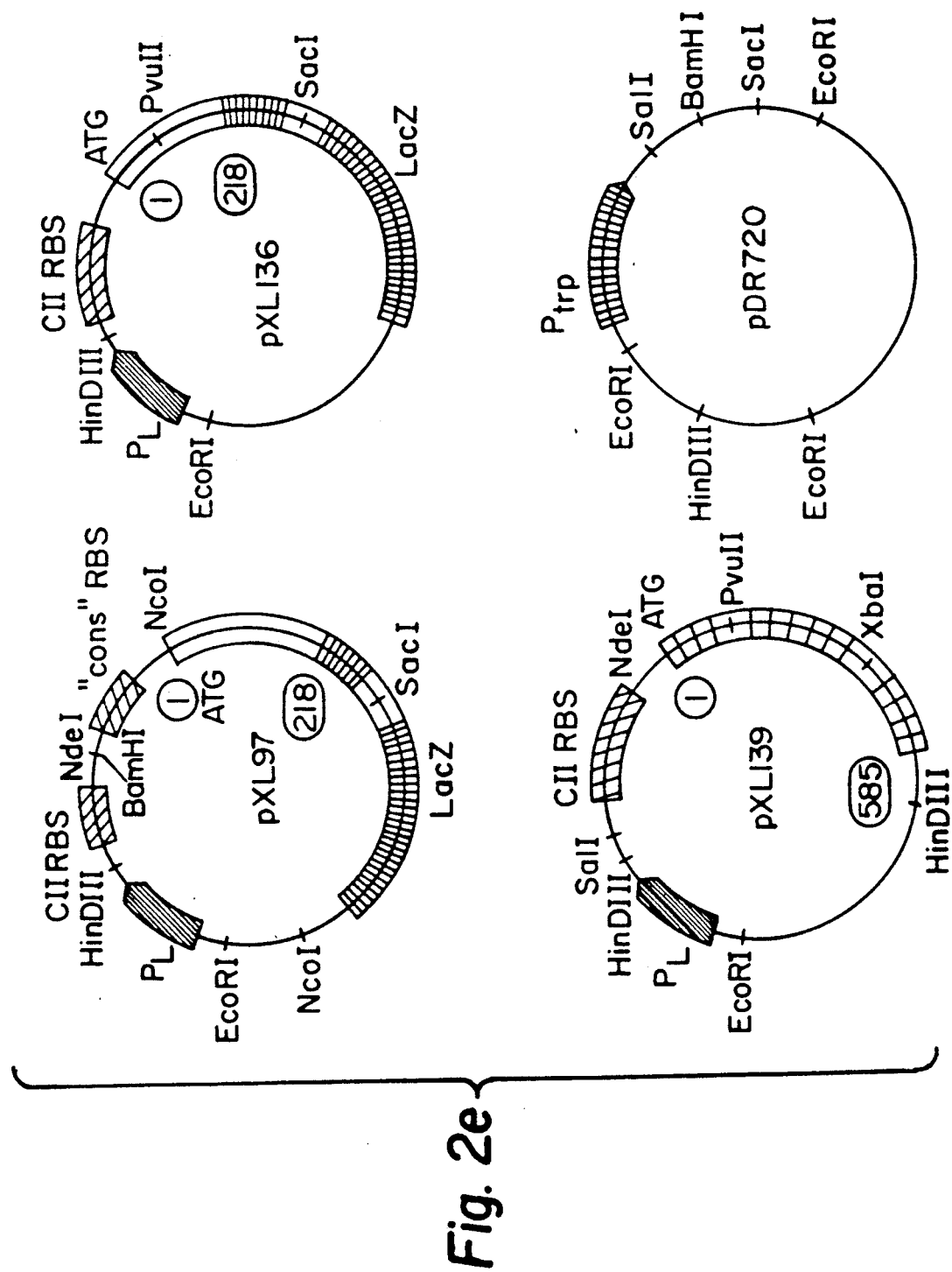
Figure 2F:
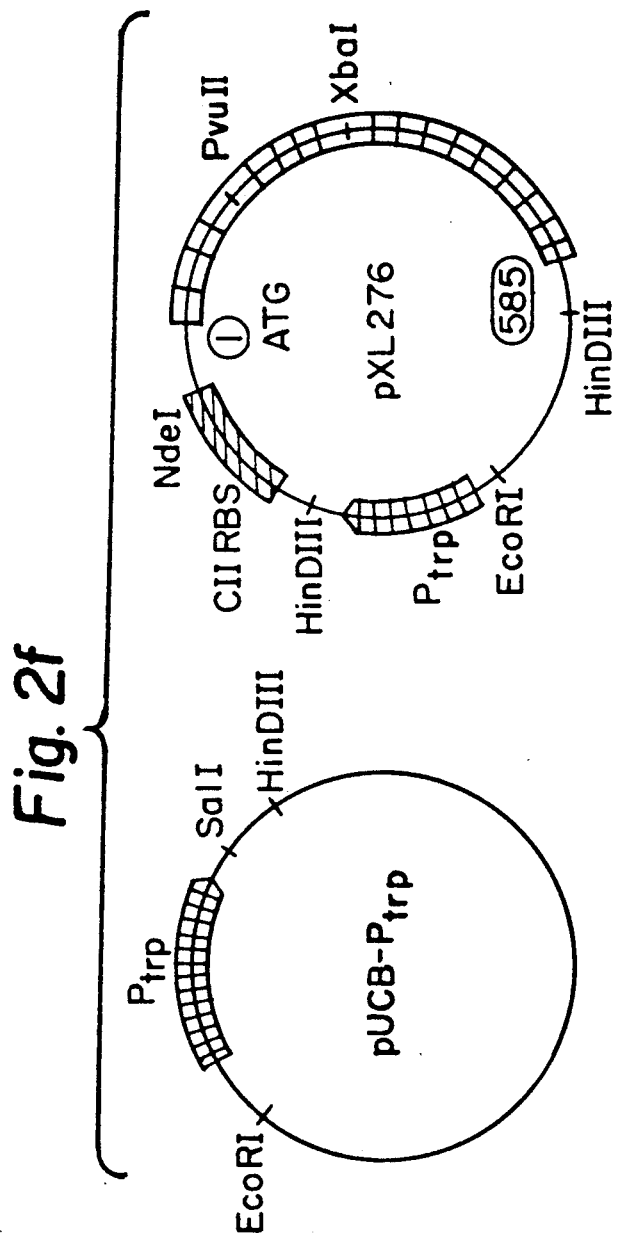

Thus, the present invention provides a process for the biosynthesis of human serum albumin in a microorganism.

To achieve this objective the structural gene for human serum albumin is modified in vitro in such a manner that it possesses an initiation codon, and the modified structural gene is then linked to an inducible regulator gene. Culture of a host bacterium, such as *E. coli*, containing the modified gene produces a substantial level of albumin after induction under defined conditions.

R.G. Schoner et al., Biotechnology (1985), p. 151 et seq. have observed that heterologous proteins synthesized at high level in *E. coli* are present in the cell in the form of insoluble aggregates. This same phenomenon is observed in the case of human serum albumin synthesized by *E. coli*. The insolubility of the human serum albumin produced by *E. coli* can be explained, for example, by the fact that the protein might not be synthesized in its native conformation, in particular because the intracellular oxidoreduction potential is incompatible with the correct formation of the 17 disulphide bridges in the protein (J. Uren, International Biotechnology Laboratory, April 1985, p. 26 et seq.). It has been shown in other systems that incorrectly folded proteins tend to aggregate and precipitate [J. London et al., Eur. J. Biochem (1974), 47, p. 409 et seq.; G. Orsini and M.E. Goldberg J. Biol. Chem. (1978), 253, p.3453 et seq.]. As a result, the human serum albumin synthesized in *E. coli* cannot be purified by classical methods and is not a product which can be directly used in therapy.

Many proteins can be converted to their native form after controlled denaturation and controlled reduction in vitro. This is the case, for example, with *E. coli* tryptophanase and with chymotrypsinogen, carbonic anhydrase, ribonuclease, lysozyme and trypsin inhibitor from bovine pancreas [J. London et al., Eur. J. Biochem. (1974), 47, p. 409 et seq.; G. Orsini and M.E. Goldberg, J. Biol. Chem. (1978), 253, p. 3453 et seq.; R.F. Goldberg et al., J. Biol. Chem. (1970), 9, p. 5015 et seq.; T.E. Creighton, J. Mol. Biol. (1974), 87, p. 563 et seq.]. In most of these cases, the most sensitive indicator of complete renaturation of a protein is its enzymatic activity. However, it has not been possible to demonstrate beyond question an enzymatic activity for serum albumin. The renaturation of bovine serum albumin [J. M. Teale and D.G. Benjamin, J. Biol. Chem. (1976), 251, p. 4603 et seq.] and human serum albumin [A. Wichman et al., Eur. J. Biochem. (1977), 79, p. 339 et seq.] has been possible using immunological techniques employing polyclonal antibodies. More recently, it has been shown that some monoclonal antibodies can serve as probes for the native conformation of a protein [L. Djavadi—Ohaniance et al., Biochemistry (1984), 23, p. 97 et seq.]. It is hence possible to analyse the conformation of human serum albumin using monoclonal antibodies directed against this protein, such antibodies being described in the literature [C. Lapresle and N. Doyen, Mol. Immunol. (1983), 20, p. 549 et seq.].

The present invention also provides a process For modifying the conformation of insoluble human serum albumin, obtained microbiologically by the process of the present invention or by any other method which leads to a non-native human serum albumin so as to restore the native conformation. This is achieved by denaturation using a combination of chaotropic and reducing agents and controlled renaturation, so that the protein obtained possesses a three-dimensional structure identical to that of native human serum albumin of natural origin.

In the following, the technical terms used in molecular biology have their usual meaning [see, for example, "Molecular Biology of the Gene", by J. Watson, (French edition, Intereditions 1978)]. The construction of the human serum albumin gene, the processes used for its expression, and the renaturation of the insoluble human serum albumin will be described successively.

EXPERIMENTATION

A. CONSTRUCTION OF THE HUMAN SERUM ALBUMIN GENE

1. Preparation of liver messenger RNA

Liver cells are used, obtained, for example, by biopsy, and the messenger RNA is extracted therefrom according to the method described, for example, by V. Glisin et al., Biochemistry (1974), 13, p. 2633 et seq.; and by R. Deeley et al., J. Biol. Chem. (1977), 252, p. 8310 et seq.. The cells obtained by the biopsy are treated with 6M guanidine thiocyanate solution and the total RNA is purified by several cycles of precipitation in ethanol at $-20°$ C., centrifugation and redissolution of the centrifugation pellets.

The preparation is enriched in messenger RNA by several cycles of affinity chromatography on columns of oligo(dT)-cellulose according to the technique described by H. Aviv and P. Leder, Proc. Natl. Acad. Sci. (USA) (1972), 69, p. 1408 et seq.. The messenger RNA thus isolated, containing 1 to 2% of total RNA, is stored in aqueous solution at $-70°$ C.

It is possible to determine the proportion of messenger RNA specific for human serum albumin within the total population (for example by in vitro translation of an aliquot of the RNA solution in rabbit reticulocyte lysates). One method consists in using the reticulocyte lysate supplied by Amersham, following the procedure recommended by this supplier. Thus, it is possible to determine the fraction of newly formed protein which is immunoprecipitable by anti-albumin antibodies within the whole group of newly formed proteins. A fraction, for example, of the order of 6% is obtained.

2. Synthesis of cDNA and cloning in *E. coli*.

a. Synthesis of the first strand

Starting with a modification of the technique of G.N. Buell et al., J. Biol. Chem. (1978), 253, p. 2471 et seq., 5 $\mu$g of total messenger RNA, for example, are used in a final volume of 50 microliters of a solution containing: 100 mM Tris.HCl pH 8.3, 10 mM $MgCl_2$, 0.4 mM DTT, 20 mM KCl, 0.4 mM Na pyrophosphate, 1 mM with respect to each nucleotide triphosphate (dNTP), 100 $\mu$g/ml of oligo(dT)$_{12-18}$, 0.5 U/ml of ribonuclease inhibitor, 50 picomoles of radioactive tracer and 40 units of reverse transcriptase (Life Sciences, Inc.).

The reaction of reverse transcription of the messenger RNA to the complementary DNA (cDNA) takes place for 1 hour at 42° C.

The extent of synthesis of cDNA is calculated by measuring the level of incorporation of the radioactive tracer into acid-precipitable molecules, according to a known technique e.g. as described by Maniatis et al, "Molecular Cloning - A laboratory manual", Cold Spring Harbor Laboratory (1982), p. 230 et seq.".

After 1 hour, the reaction is stopped by adding EDTA (20 mM), and the messenger RNA is destroyed by alkaline digestion in 50 mM NaOH at 42° C. for 3 hours.

The newly formed cDNA is separated from the nonincorporated dNTPs and the alkaline degradation products of the RNAs by chromatography, for example, on a column of Sephadex G100 (Pharmacia Fine Chemicals). 1.5 μg of single-stranded cDNA is obtained from 5 μg of total messenger RNA.

b. Synthesis of the second strand

The single-stranded cDNA is converted to double-stranded DNA by the action of the "Klenow" fragment of DNA polymerase I.

The reaction conditions are: 100 mM Hepes pH 7, 10 mM $MgCl_2$, 2.5 mM DTT, 70 mM KCl, 0.5 mM with respect to each dNTP and 50 units of DNA polymerase I "Klenow" fragment (marketed, for example, by New England Biolabs Inc.).

The reaction is carried out for 15 hours at 15° C., and the double-stranded DNA is separated from the nonincorporated dNTPs again by chromatography on a column of Sephadex G100.

c. Cloning of the double-stranded DNA

To eliminate the single-stranded DNA molecules and obtain a blunt-ended double-stranded DNA, the unpaired sequences are treated with $S_1$ nuclease according to the technique described by A. Efstradiatis et al., Cell (1976), 7, p. 279 et seq.. The double-stranded newly formed DNAs are separated according to their size by centrifugation in a sucrose gradient. In general, a gradient of 5%-20% of sucrose in 50 mM Tris.HCl pH 8.5, 10 mM EDTA, 800 mM NaCl is used, centrifuged at 210,000 g for 15 hours at 20° C., and the gradient is fractionated into aliquots after centrifugation.

The size of the molecules in each fraction is monitored by electrophoresis of samples carried out in parallel with DNA standards of known sizes, and the fractions containing a DNA consisting of a chain of more than 500 base pairs are combined.

For the purpose of cloning this DNA, its 3' ends are first elongated with oligo(dC) and, in parallel, the 3' ends of the PstI site of the plasmid vector pBR322 are elongated with oligo(dG) according to the technique of F. Rougeon et al., J. Biol. Chem. (1977), 252, p. 2209 et seq..

The double-stranded DNA described above is then hybridized with the plasmid vector, for example according to the technique of L. Villa-Komaroff et al., Proc. Natl. Acad. Sci. (USA) (1978), 75, p. 3727 et seq..

A "library" of liver cDNA clones is created by transformation of E. coli bacteria with this hybridized DNA, according to the method described by M. Mandel and A. Higa, J. Mol. Biol. (1970), 53, p: 154 et seq., and M. Dagert and S.D. Erlich, Gene (1979), 6 p. 23 et seq..

d. Identification of the albumin cDNA clones

A colony hybridization technique is employed, using synthetic bligonucleotides the sequences of which are deduced from the protein sequence of human albumin [B. Meloun et al., FEBS Letters (1975), 58, p. 134 et seq.; M. Grunstein and D. Hogness, Proc. Natl. Acad. Sci. (USA) (1975), 72, p. 3961 et seq.; R.B. Wallace et al., Nucleic Acids Res. (1981), 9 p. 879 et seq.].

The clones are cultured in series of 96 on nitrocellulose filters in series of 96 in Luria medium containing 25 μg/ml of tetracycline placed in square dishes. After growth at 37° C. followed by amplification in the presence of 250 μg/ml of chloramphenicol, the colonies cells in the cell obtained are lysed with sodium hydroxide and DNA from the lysed cells is then hybridized with oligonucleotides which have been radioactively labelled at position 5' by kinase treatment, in a solution containing: 5×SSC, 0.5% NP 40, 100 μg/ml of salmon sperm DNA denatured by boiling and cooled rapidly in ice, and 0.5 ng/ml of kinase-treated oligonucleotide. The hybridization is performed at 37° C. for 18 hours. The filters are then washed in 5×SSC at 25° C., then at 37° C. and then at 45° C., this being done four times for 15 minutes at each stage.

The filters are then exposed at −70° C. to Kodak X-OMAT film with an enhancing screen for 15 to 24 hours. The clones which hybridize with the probes are re-isolated and then lysed. The plasma DNA is purified by centrifugation in caesium chloride/ethidium bromide medium according to a known technique.

The DNA of the insertion is sequenced by the Maxam-Gilbert technique [A. Maxam and W. Gilbert, Methods Enzymol. (1980), 65, p. 499 et seq.]to compare the protein sequence derived from the nucleotide sequence with that of human serum albumin.

In this manner a series of clones is identified in which the insertions correspond to the whole human serum albumin gene.

FIG. 1 shows the restriction map of the serum albumin gene, as well as the position of three of the most representative insertions, designated "pT1B11", "pAA38" and "p6D8".

e. Incorporation of an initiation codon into the structural gene (FIG. 2)

a) The DNA of plasmid "pT1B11" is digested with the enzymes PstI and PvuII, and an 0.3 Kbp base-pair DNA fragment is isolated containing to the sequence of the 5' end of the serum albumin gene and including the nucleotides coding for (amino acids Nos. 1 to 58). At the PvuII end, a junction sequence is attached consisting of the site for recognition of the enzyme BamHI. A PstI-BamHI fragment is thereby obtained.

A synthetic oligonucleotide 21 bases long is prepared separately, the oligonucleotide possessing an "ATG" triplet in front of the nucleotides which code for the amino acids of human serum albumin and also an NcoI restriction site, and its sequence being as follows: 5'GAATCCATGGATGCACACAAG 3'.

The PstI-BamHI DNA fragment is denatured and hybridized with the synthetic oligonucleotide. The hybridization is accomplished through the sequence 5'. . . GATGCACACAAG 3', the 3' end of the complementary DNA strand being unpaired. The unpaired ends are digested and polymerization is then carried out in the 5'. . . 3' direction with DNA polymerase I Klenow fragment, according to the techniques of H. Jacobsen et al., Eur. J. Biochem. (1974), 45, p. 623 et seq..

A fragment is thereby obtained containing an NcoI site followed by the ATG triplet at the 5' end and a BamHI site at the 3' end.

b) The ligation is carried out of three DNA fragments:

1) an EcoRI-BamHI fragment of plasmid "pLG200" [L. Guarente et al., Cell (1980) 20, p. 543 et seq.] carrying a gene for resistance to antibiotics, the origin of replication and the 3' end of the β-galactosidase gene, 2) an EcoRI-PvuII fragment of plasmid "pGL101" [G. Lauer et al., J. Mol. Appl. Genet. (1981), 1, p. 139 et seq.] carrying the P$_{lac}$ promoter and the ribosome binding site (RBS) of the E. coli lacZ gene, 3) the mutagenized 0.3 Kbp DNA fragment described above which codes for the first 62 amino acids of human albumin.

A plasmid (pXL52) is isolated in which fusion of the 5' end of the human serum albumin gene with the E. coli β-galactosidase gene has been accomplished.

f. Construction of the complete gene (FIG. 2)

The DNA of plasmid "p6D8" is digested with EcoRI, and partially with BglII, according to a technique already described. The large EcoRI-BglII fragment, containing the sequence which codes for the last 405 amino acids of human serum albumin followed by the origin of replication of the plasmid and the gene for resistance to tetracycline, is isolated.

The DNA of plasmid "pXL52" described above is digested with EcoRI and Sau3A, and a fragment containing 200 base pairs is isolated.

The DNA of plasmid "pAA38" is digested with Sau3A and a fragment containing 540 base pairs is isolated.

The three fragments are ligated (in the order [p×L52 EcoRI-Sau3A]—[pAA38 Sau3A]—[p6D8 BglII-EcoRI]), turning to advantage the compatibility between the Sau3A and BglII sites. A plasmid known as "pXL53" is obtained, the quality of the construction of which is monitored by complete sequencing of the fragment between the EcoRI site and the PstI site corresponding to the junction between the insertion and the plasmid vector.

The complete nucleotide sequence, together with the derived protein sequence, are shown in FIGS. 3 and 4.

The observed variations between this sequence and the published protein sequence [B. Meloun et al., FEBS Letters (1975), 58, p. 134 et seq.; M. Dayhoff, Atlas of Protein sequence and structure (1978), 5, supplement 3, p. 306] are as follows:

| Position | Meloun et al. | Human serum albumin deduced from the sequence of "pXL53" |
| --- | --- | --- |
| 131 | Glutamine | Glutamic acid |
| 364 | Histidine | Alanine |
| 367 | Tyrosine | Histidine |
| 370 | Alanine | Tyrosine |
| 381 | Valine | Methionine |
| 464 | Glutamic acid | Histidine |
| 465 | Histidine | Glutamic acid |
| 501 | Glutamine | Glutamic acid |

B. CONSTRUCTION OF SYSTEMS FOR THE EXPRESSION OF HUMAN SERUM ALBUMIN

1. Use of bacteriophage lambda "P$_L$" promoter a) Plasmid "pXL53" is linearized by partial digestion with the enzyme NcoI, with respect only to the NcoI site at the 5' end of the initiation codon, and blunt ends are formed by filling-in according to the technique of R.M. Wartell and W.S. Reznikoff, Gene (1980), 9, p. 307 et seq..

An "adaptor" is synthesized containing at the 5' end a sequence corresponding to the recognition site for a restriction enzyme such as BamHI, followed by a sequence corresponding to a ribosome binding site ("consensus" or "theoretical" RBS). The adaptor sequence is 5'GGATCCTAGGAGGAAC 3'.

The ligation of the adaptor at the 5' end of a blunt-ended DNA has been described, for example, by C.P. Bahl et al., Gene (1976), 1 p. 81 et seq..

The method consists in performing the reaction on 10 microliters of a solution containing 50 mM Tris.HCl pH 7.5, 10 mM MgCl$_2$, 15 mM DTT, 1mM ATP, 50 μg/ml of adaptor, 20 μg/ml of DNA and 1 unit of DNA ligase (New England Biolabs Inc.). The reaction is carried out for 10 hours at 15° C. This ligation creates a BamHI site without eliminating the NcoI site.

The ligation product is digested with BamHI and with HinDIII. As a result of the presence of a HinDIII site at the 3' end of the human serum albumin gene, a DNA fragment containing the entire coding sequence is obtained.

The HinDIII-BamHI fragment thereby obtained is subcloned, for example, in plasmid "pBR322" by transforming E. coli according to the method described above to obtain plasmid "p×L61".

Plasmid "p×L61" does not contain any promoter.

Bacteriophage lambda "P$_L$" promoter is situated on the bacteriophage chromosome between a BglII site and a BamHI site [see E. Szybalski and W. Szybalski, Gene (1979), 7 p. 217 et seq.], and its nucleotide sequence is known [F. Sanger et al., J. Mol. Biol. (1982), 162, p. 279 et seq.]. This fragment can be cloned and its restriction sites modified according to known methods.

It is noted that plasmids carrying P$_L$ have to be propagated in E. coli strains carrying the repressor gene cI, in order to prevent this promoter from being expressed constitutively.

In a first construction, P$_L$ is available in the form of a BamHI fragment from plasmid "pP$_L$-lambda" (Pharmacia P.L. Biochemicals). By insertion of this BamHI fragment into the BamHI site of plasmid "p×L61", plasmid "p×L65" may be obtained, in which plasmid it has been verified that the orientation of promoter with respect to the structural gene for human serum albumin is correct.

Other constructions can be carried out from available plasmids. For example, it is possible to excise from plasmid "pP$_L$-lambda" an HaeIII-HaeIII fragment containing the P$_L$ promoter and insert it into the SmaI site of a multi-site cloning sequence carried by a plasmid, such as plasmid "pUC8" [J. Vieira and J. Messing, Gene (1982), 79, p. 259 et seq.], to obtain "pUC8-P$_L$" in which the EcoRI site is on the 5' side of the promoter.

Starting with plasmid "pPS1" [P. Sarmientos et al., Cell (1983), 32, p. 1337 et seq.], the HinDIII site closest to the NdeI site (FIG. 2) can first be destroyed and the small EcoRI-HinDIII fragment then replaced by, on the one hand the EcoRI-BamHI fragment of plasmid "pUC8-P$_L$" containing the P$_L$ promoter, and on the other hand the BamHI-HinDIII fragment of plasmid "p×L61" containing the serum albumin gene. Plasmid "p×L70" is thereby obtained, in which the assembly [P$_L$-"consensus" RBS-ATG-human serum albumin gene] is carried on an EcoRI-HinDIII DNA fragment.

b) Replacement of the "consensus" RBS by that of the CII gene of bacteriophage lambda The CII gene of bacteriophage lambda, the sequence and the initiation site of which are known [E. Schwarz et al., Nature (1978), 272, p. 410 et seq.], can be efficiently translated.

A plasmid is constructed containing the expression system ["$P_L$" promoter—CII RBS—ATG—serum albumin gene].

For example, after the BamHI site of "pUC8-$P_L$" has been destroyed by the action of SI enzyme [A.J. Berck and P.A. Sharp, Cell (1977), 12, p. 721] an EcoRI-HinDIII fragment can be isolated containing the $P_L$ promoter, and the fragment can then be linked with an EcoRI-HinDIII fragment of plasmid "pDS20" [G. Duester et al., Cell (1982), 30, p. 855 et seq.] to obtain plasmid "p×L73".

The CII gene RBS is extracted from plasmid "pPS1". This plasmid is digested with NdeI and a BamHI adaptor is inserted after the formation of blunt ends. The RBS is then excised in the form of a HinDIII-BamHI fragment.

A plasmid "p×L88" in which this HinDIII-BamHI fragment is linked with the large HinDIII-BamHI fragment of plasmid "p×L73" is constructed first. In the new plasmid "p×L88", the CII RBS is inserted in the correct orientation with respect to the $P_L$ promoter, and the whole combination is present in a multi-site system in such a way that the $P_L$-CII RBS assembly is carried on a 578 base-pair EcoRI-BamHI DNA fragment.

The 578 base-pair EcoRI-BamHI fragment is sub-cloned between the EcoRI and BamHI sites of plasmid "pMC1403" [M.J. Casadaban et al., J. Bacteriol. (1980), 143, p. 971 et seq.] which carries the β-galactosidase gene (lacZ) after the BamHI site. This construction leads to plasmid "p×L91" in which the β-galactosidase gene is expressed under the control of the [$P_L$-CII RBS]system.

The BamHI-BglII fragment of plasmid "p×L61" described above is sub-cloned in the BamHI site of plasmid "pMC1403". (The ligation of a BglII site in a BamHI site is possible, but excision by BamHI at BglII is no longer possible; there consequently remains only one BamHI site).

This construction ("p×L71") leads to the insertion of a 700base- pair DNA fragment containing the sequence [BamHI-"consensus" RBS-ATG-NcoI-partial gene for serum albumin (coding for amino acids 1 to 218) -β-galactosidase gene].

This plasmid is cut with BamHI and SacI (the SacI site is present in the β-galactosidase gene) and inserted in plasmid "p×L91" described above in place of the preexisting BamHI-SacI fragment.

This then leads to plasmid "p×L97" in which the insertion has the following structure: [EcoRI site—$P_L$—CII RBS—BamHI site—"consensus" RBS—NcoI site—ATG—partial gene for serum albumin—β-galactosidase gene].

Plasmid "p×L97" is digested with BamHI, and partially with NcoI with respect only to the NcoI site near to the initiation codon, and blunt ends are formed by the action of $S_1$ nuclease, and the plasmid is then closed up again. This manipulation on the one hand eliminates the "consensus" RBS DNA sequence, and on the other hand brings an ATG of the CII RBS into phase with the serum albumin sequence.

Plasmid "p×L136" is thereby obtained, which contains the sequence [EcoRI site-$P_L$-CII RBS-ATG-partial gene for serum albumin-β-galactosidase gene].

Since the partial gene for serum albumin possesses a PvuII site, plasmid "p×L136" is digested with EcoRI and PvuII, and a 760 base-pair fragment is extracted and inserted between the EcoRI and PvuII sites of plasmid "p×L70" described above. Plasmid "p×L139" is thereby obtained, which carries the structure [$P_L$-CII RBS-complete serum albumin gene] on an EcoRI-HinDIII fragment, like plasmid "p×L70", and which carries the substitution of the "consensus" RBS by that of the CII gene.

c) Expression of serum albumin after induction of the "$P_L$" promoter

Inoculation is carried out of an isolated *E. coli* colony carrying the temperature-sensitive repressor gene of the "$P_L$" promoter (cI$^{ts}$ gene) and transformed by one of the plasmids "p×L65", "p×L70" and "p×L139".

When the bacterium is in exponential phase, the "$P_L$" promoter of the plasmid is induced by raising the incubation temperature very rapidly to 42° C. Incubation is continued for 90 minutes. A sample of the culture is withdrawn and the bacteria are lysed in a suspension containing 60 mM Tris.HCl pH 6.8, 2% SDS, 100 mM β-mercaptoethanol, 10% of glycerol and 0.1% of bromophenol blue for 5 minutes.

The proteins are separated by polyacrylamide gel electrophoresis according to the method of U.K. Laemli, Nature (1970), 227, p. 680 et seq. or that of K. Weber and M. Osborne, J. Biol. Chem. (1969), 244, p. 4406 et seq..

The proteins are transferred to a nitrocellulose . filter [M. Bittner et al., Anal. Biochem. (1980) 102, p. 459 et seq.; E.J. Sbellwsag and A.E. Dahlberg, NucleidAcid Res. (1980), 8, p. 229 et seq.). The presence of human albumin is detected by immunology, either with antibodies to human albumin followed by binding of labelled protein A, or with biotin-labelled anti-albumin antibodies visualized by means of avidin-peroxydase complexes.

In this manner, the presence is demonstrated of a protein which reacts with antibodies to human albumin, which co-migrates with authentic albumin and which is only present in lysates of *E. coli* after induction of this bacterium at 42° C. in the presence of plasmid "p×L65", "p×L70" or "p×L139".

The level of human serum albumin produced under these conditions can be determined. The proportion of albumin reproducibly produced is of the order of 0.1% of the total proteins demonstrated in an *E. coli* lysate under denaturing conditions.

2. Use of the promoter of the *E. coli* tryptophan operon ($P_{trp}$) to replace the "$P_L$" promoter The introduction of the structural gene for human serum albumin behind an inducible bacterial promoter enables this protein to be expressed in *E. coli*. The levels of expression of the different systems described above are close to each other, and of the order of 1000 molecules of serum albumin per cell. These results are close to those obtained with similar systems such as those described in European Patent Applications EP 73,646 and EP 91,527. In particular, in European Patent Application EP 91,527, a maximum yield of 8,000 molecules per cell of a "polypeptide resembling human serum albumin" is noted. The protein obtained is not strictly identical to human serum albumin, and the levels produced are incompatible with the demands of industrial productivity. Moreover, the production of serum albumin is accompanied by a lethal effect of the producing bacterium.

It has now been found, and this forms the subject of the present invention, that the production of human serum albumin can be considerably improved by using a plasmid comprising an inducible promoter, a ribosome binding site of a gene which is translated efficiently, and a human serum albumin gene possessing an ATG initiation codon at the 5' end.

More especially, the invention provides a process for preparing human serum albumin by culturing a bacterium, such as *E. coli*, containing a plasmid comprising as promoter, the tryptophan operon ($P_{trp}$), the ribosome binding site of the CII gene of bacteriophage lambda not containing the $t_{R1}$ transcription termination sequence, and a human serum albumin gene.

The promoter of the *E. coli* tryptophan operon enables the expression of a gene to be induced when the *E. coli* strain is cultured in the absence of tryptophan or in the presence of an analogue such as 3-indolylacrylic acid [C. Yanofsky et al., Nucleic Acids Res. (1981), 9, p. 6647 et seq.]. Such a promoter is available in plasmids such as "pDR720" (Pharmacia $P_L$Biochemicals) [also see D. Russel and G. Bennett, Gene (1982), 20, p. 231 et seq.].

The construction of a plasmid containing the system lPtrp-CII RBS-human serum albumin gene] can be carried out in the following manner:

The EcoRI-SalI fragment of plasmid "pDR270" containing the $P_{trp}$ promoter is inserted between the EcoRI and SalI sites of "pUC8". Plasmid "pUC8-Ptrp" is thereby obtained.

Plasmid "p×L139" described above is cut at the single SalI site between the $P_L$ promoter and the CII RBS. The DNA is digested with the enzyme Bal31 in such a way that the transcription termination site $t_{R1}$ on the 5' side of the CII RBS is digested, a HinDIII adapter is then added and the HinDIII-XbaI fragment, containing the CII RBS from which $t_{R1}$ has been cleaved and the first 357 codons of the human serum albumin gene, is isolated. This HinDIII-XbaI fragment is combined with, on the one hand the XbaI-EcoRI fragment of plasmid "p×L139" containing the end of the human serum albumin gene, and on the other hand the EcoRI-HinDIII fragment carrying the $P_{trp}$ promoter of plasmid "pUC8-$P_{trp}$".

Plasmid "p×L276" is thereby obtained. This plasmid now only contains 41 nucleotides of the CII RBS upstream of the ATG starting codon of the human serum albumin gene.

C. EXTRACTION AND RENATURATION OF THE HUMAN SERUM ALBUMIN SYNTHESIZED BY *E. COLI*

1. Production culturing

Strain G1381 is used, for example, this strain deriving from *E. coli* strain B54125 (available from the Institut Pasteur Collection, Paris, France) by transformation with plasmid "p×L276" following the method described by M. Mandel and A. Higa [J. Mol. Biol. (1970), 53, p. 154 et seq.]. Plasmid "p×L276" contains the functional gene for human serum albumin under the control of the promoter of the tryptophan operon ($P_{trp}$). The expression of human serum albumin is consequently induced when the bacterium is cultivated in the absence of tryptophan or in the presence of an analogue such as 3-β-indoleacrylic acid [B.P. Nichols and C. Yanofsky, Methods Enzymol. (1983), 101, p. 155 et seq.].

The following procedure can be adopted. Starting with a recent re-isolation of strain G1381 in a Petri dish containing agar based on LB medium [10 g of Bacto-tryptone (Difco), 5 g of Bacto Yeast Extract (Difco) and 5 g of NaCl per liter of distilled water] containing 50 μg/ml of ampicillin (LBAp), a pre-culture is prepared in LBAp medium at 37° C. with agitation for 16 hours. This pre-culture is then used for seeding at a dilution of 1/100 a synthetic medium without tryptophan [for example M9 medium with glucose +0.1% casamino acids according to J.H. Miller, "Experiments in Molecular Genetics", Cold Spring Harbor Laboratory, New York, (1972), p. 431 et seq.]. The production culturing is carried out at 37° C. so as to optimize the yield of human serum albumin per liter of culture. Under laboratory conditions (culturing in an Erlenmeyer), the cells are harvested towards the end of the exponential phase, after approximately 6 hours of culture. The turbidity is then between 3 and 4 optical density units at 610 nm. The yields obtained are of the order of 5 to 10 mg of serum albumin per liter of culture and per optical density unit at 610 nm, which represents approximately 5 to 7% of the total proteins (see FIG. 5).

2. Rupture of the cells and recovery of the insoluble albumin

After production culturing, the cells are collected and lysed, for example by centrifugation and sonication. On the laboratory scale, a Branson sonicator (Proscience, France, Model B30) can be used after the cells have been concentrated 20- to 30-fold in PBS buffer (0.2 g/l KCl, 0.2 g/l KH$_2$PO$_4$, 8 g/l NaCl, 1.25 g/l Na$_2$HPO$_4$). The rupturing of the cells is performed at 0° C. in the continuous mode (1 to 2 bursts each lasting 4 to 6 minutes, depending on the cell density). A concentrated cell suspension can also be pretreated in the presence of 1 mg/ml of eggwhite lysozyme for 10 to 20 minutes at room temperature before sonication.

Under these conditions, the human serum albumin is almost completely insoluble; it is hence possible to achieve, at this point, a substantial purification of this protein by centrifuging the cell lysate and recovering only the centrifugation pellet obtained after a washing cycle in PBS buffer. The human serum albumin then represents from 30 to 50% of the insoluble proteins present in the pellet.

3. Solubilization of the human serum albumin by denaturation/reduction

The serum albumin thereby obtained can be completely solubilized, under reducing conditions, by high concentrations of a chaotropic agent such as 8M urea or 6M guanidine HCl. It is known from the literature (G. Orsini and M.E. Goldberg, see above) that such conditions bring about complete denaturation of the polypeptide chain to the randomly coiled state and a reduction of all the inter- and intramolecular disulphide bridges. More especially, if the "sonication pellet" described above is taken up in a buffer containing 6M guanidine HCl, 0.1M KH$_2$PO$_4$, pH 7.5 and 0.1M β-mercaptoethanol, such that the serum albumin originating from *E. coli* is present at concentrations of the order of 1–5 mg/ml in this solution ("denaturation solution") and if the suspension obtained is left gently agitated in a closed vessel for approximately 16 hours at 4° C., an almost clear solution is obtained. The insoluble residues can then be simply removed by centrifugation or filtration.

4. Renaturation of the human serum albumin obtained microbiologically a. Determination of the renaturation conditions

Figure 6A:
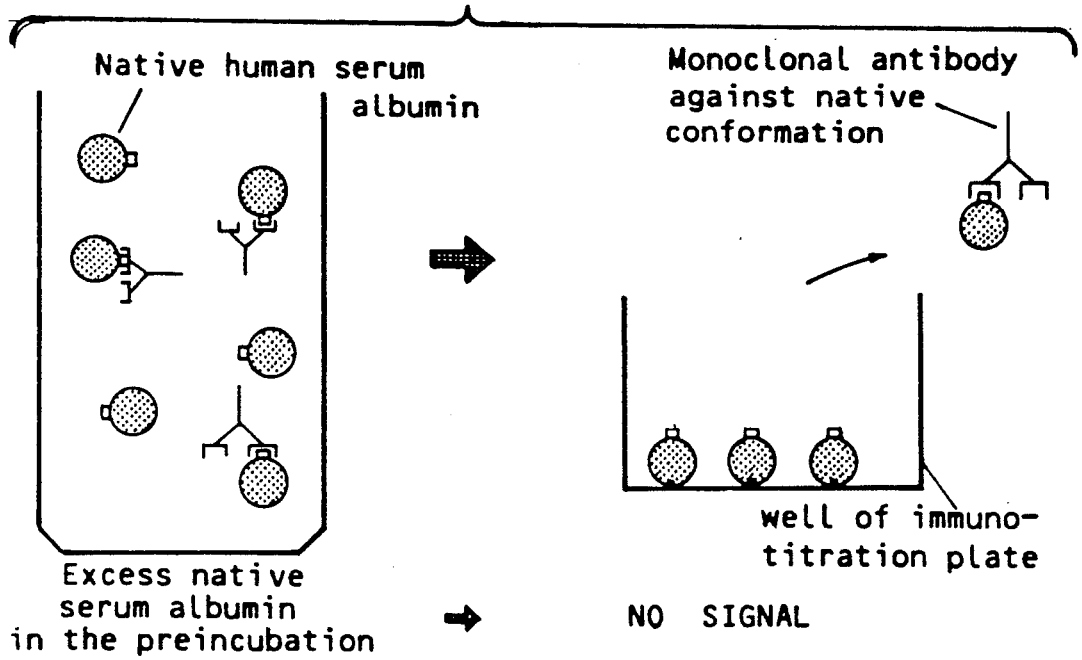
Figure 6B:
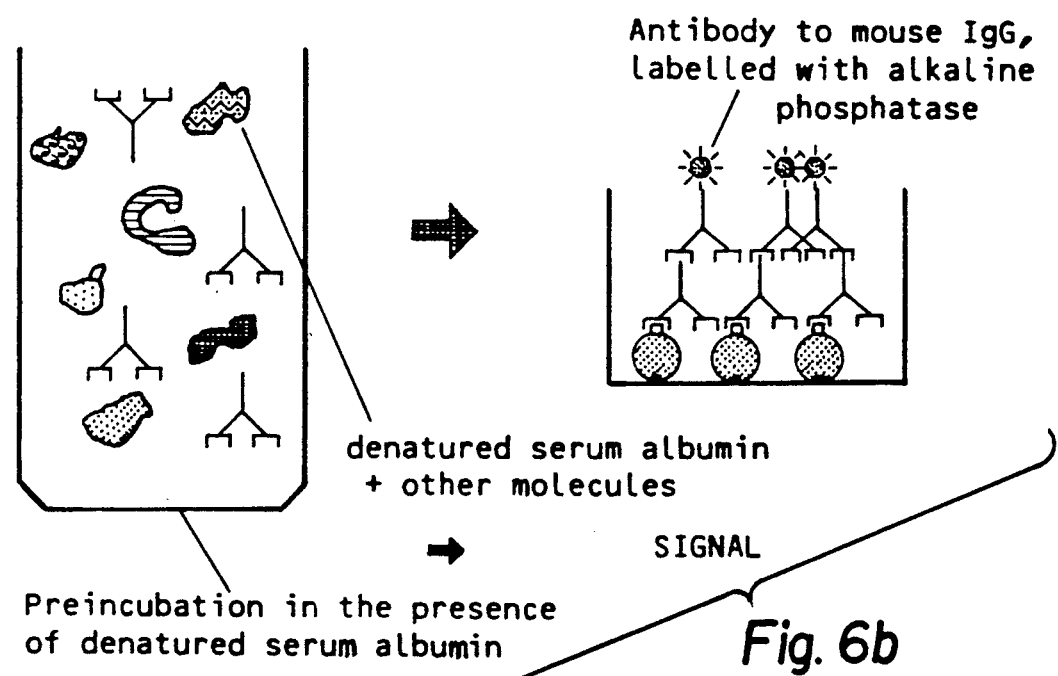

In order then to permit the molecule to regain its native conformation, it is necessary to remove or reduce the concentrations of the denaturing and reducing agents. It is possible, for example, to dilute the denatured/reduced fraction in buffers which permit renaturation. It is possible to assess the degree of renaturation of the protein by means of an ELISA assay method according to the technique of L. Ohaniance et al. (see above), using the monoclonal antibodies directed against serum albumin which have been described by Lapresle and Doyen (see above). The principle of such a method is as follows (FIG. 6). Native serum albumin is bound to a well in a microtest plate. In another tube, the antibody chosen for the analysis is mixed with a range of concentrations of the product to be examined. After incubation, the mixture is introduced into the well. The presence of the antigenic unit corresponding to the monoclonal antibody in the initial mixture inhibits the binding of this antibody to the human serum albumin adhering to the well. In a second stage, the presence of the monoclonal antibody bound in the well is revealed by means of a second antibody coupled to an enzyme activity: the intensity of the signal detected will hence, under certain conditions, be inversely proportional to the concentration of specific antigen in the solution analyzed. A detailed description of the method is given below under b.

A control preparation of commercial serum albumin, denatured, reduced and treated with excess N-ethylmaleimide, is used to distinguish between a monoclonal antibody specific for the primary sequence of human serum albumin and an antibody specific for the native conformation of the protein. It can be seen from Table 1 that, for example, the monoclonal antibody HA4 is "sequence-specific", whereas HA9 recognizes the native protein without recognizing denatured and reduced serum albumin. It also emerges from this table that, in the suspension of a sonicated lysate pellet of a culture of strain G1381 induced in minimal medium, the presence of antigenic material is detected by HA4 but not by HA9. This is compatible with the hypothesis that the HSA manufactured by *E. coli* is not in the native conformation characteristic of serum albumin of natural origin.

TABLE 1

IDENTIFICATION OF THE MONOCLONAL ANTIBODIES SPECIFIC FOR THE NATIVE CONFORMATION OF SERUM ALBUMIN: EXAMPLE OF HA9
For a given concentration of antigen: $OD_{420}$

|  | HA4 | HA9 |
|---|---|---|
| BSA native | 0.415 | 0.667 |
| HSA denatured, reduced, treated with NEM | 0.104 | 0.734 |
| HSA native | 0.063 | 0.007 |
| HSA *coli* before renaturation | 0.032 | 0.810 |
| HSA *coli* after renaturation | 0.055 | 0.021 |

Abbreviations:
BSA: bovine serum albumin
HSA: human serum albumin
NEM: N-ethylmaleimide If a method is available for assaying the antigens characteristic of the native conformation, it becomes possible to estimate the efficacy of the renaturation conditions, expressed in the form of a renaturation yield. This renaturation yield is equal to R/T, where R is the concentration of renatured protein calculated from a calibration curve obtained with the same monoclonal antibody and native serum albumin, and T is the total concentration of serum albumin of microbiological origin. This latter concentration is calculated by comparing the staining with Coomassie blue on SDS-polyacrylamide gel of the band corresponding to the serum albumin in the sample in question, with respect to a range of serum albumin concentrations under the same conditions.

The important parameters for the renaturation of recombinant human serum albumin can then be studied: nature of the buffer used, pH, ionic strength, presence of chelating agents, temperature, renaturation time, optimal concentration of albumin during the renaturation phase, and the like.

More especially, the renaturation of serum albumin of microbiological origin can be obtained under the following conditions, which were adopted after a series of optimizations:

50 mM Tris.HCl pH 8.5
100 mM NaCl
1 mM EDTA

If the denatured serum albumin is diluted 100-fold and reduced in this "renaturation solution", the albumin remains soluble and, after 10 to 15 hours at 4° C., a renaturation yield is obtained greater than 90% if the concentration of serum albumin during the renaturation is less than 50 mg/l. The solution thereby obtained has a slight whitish opalescence, which can be eliminated by centrifugation or filtration. The precipitate thereby obtained contains, in particular, two *E. coli* proteins which represent the major protein contamination of the serum albumin in the insoluble fraction of the cell lysate. Consequently, at the same time as the renaturation, a stage of substantial purification is effected, inasmuch as the serum albumin now represents 80 to 90% of the protein material.

The serum albumin, which is entirely present in the soluble fraction of the renaturation mixture, can be concentrated by several methods; some of these methods can serve simultaneously as a purification stage. In order to have recourse to a product, the concentration of which is compatible with subsequent analyses, the renatured serum albumin can also be concentrated by ultrafiltration, using commercially available devices. In this way, a solution is obtained containing renatured serum albumin at a concentration of the order of 1 mg/ml.

b. Description of the ELISA assay method

Monoclonal antibodies were supplied by Professor Lapresle (C. Lapresle and N. Doyen, see above).

A denatured human serum albumin is prepared as follows to serve as a negative control in the renaturation experiments. After incubation for 16 hours at 4° C. with gentle agitation, a solution of human serum albumin (Sigma) at 1 mg/ml in the "denaturation solution" is diluted 100-fold in the "renaturation solution". 1/100 of the volume of 0.5M N-ethylmaleimide (in water) is added immediately. The solution thereby obtained is dialyzed against the same buffer ("renaturation solution") and then stored at 4° C.

Native human serum albumin is adsorbed in the wells of a microtitration plate (Nunc Immuno Plate type II) by incubating for 16 hours at 4° C. the plates containing 200 μl per well of a solution at 0.1 mg/ml of the protein in a 0.1M sodium carbonate buffer, pH 9.5. The plates are then washed three times with a buffer containing 20 mM Tris.HCl pH 7.5, 150 mM NaCl and 1 mM EDTA.

In each case, the optimum concentration of monoclonal antibody is determined. In the case of the experiments described above, the antibodies used were diluted from 1/1000 to 1/2500 in the buffer described above.

85 µl of the antibody dilution are mixed with an equal volume of the serum albumin solution to be examined. The mixture is incubated at room temperature for 15 minutes.

100 µl of this mixture are deposited in a pretreated well. The plate is incubated for one hour at room temperature.

After the plate is washed, 100 µl of an appropriate dilution of a second antibody (antibody to mouse IgG, coupled to alkaline phosphatase; Biosys, Compiègne, France) are introduced. The plate is again incubated for one hour at room temperature.

After the plate is washed, 150 µl of para-nitrophenyl phosphate (PNPP), at 5.2 µg/ml in a buffer containing 100 mM Tris.HCl pH 7.5 and 1.35M NaCl, are added. The enzyme reaction is stopped by adding 50 µl of 1M $K_2HPO_4$ when the intensity of the colour developed is sufficient. The optical density is then measured at 450 nm.

c. Analysis of the recombinant human serum albumin

The recombinant human serum albumin obtained after renaturation can be analyzed by various techniques described in the literature, such as polyacrylamide gel electrophoresis, electrofocusing or various types of chromatography, under non-denaturing conditions which make these techniques very sensitive to the conformation of the protein being studied. In this manner, it is possible to observe that this protein possesses characteristics very similar to those of the natural product (see FIG. 7). On the other hand, sequencing of the N-terminal end of the protein produced in this way shows the preponderant presence of a methionine as the first residue.

The human serum albumin produced by E. coli, and prepared by the process according to the invention, only differs from human serum albumin having the amino acid sequence reported for natural human serum albumin by Meloun et al. (loc. cit.) in the ways listed above and by the presence of a methionine at the N-terminal end. This protein is, moreover, obtained in a significantly improved yield, and without a lethal effect on the producing bacterium.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the microbiological preparation of human serum albumin, which comprises: culturing E. coli strain containing, and capable of maintaining, a plasmid comprising the promoter of the tryptophan operon, $P_{trp}$, the ribosome binding site of the CII gene of bacteriophage lambda not containing the $t_{R1}$ transcription termination sequence, and a human serum albumin gene containing an ATG initiation codon at the 5' end; recovering the human serum albumin produced in denatured, insoluble form and converting it into human serum albumin having the native conformation, by subjecting the said denatured, insoluble human serum albumin to the action of a chaotropic agent and a reducing agent to convert it into water-soluble form and then removing the said agents from the aqueous solution obtained to permit a rearrangement to the native conformation of the secondary and tertiary structures of the polypeptide chain of the said albumin.

2. Process according to claim 1, wherein the bacterium is a strain of E. coli.

3. A plasmid comprising the $P_{trp}$ promoter, the ribosome binding site of the CII gene of bacteriophage lambda not containing the $T_{R1}$ transcription termination sequence, and a human serum albumin gne possessing an ATG initiation codon at the end 5' end.

4. A plasmid according to claim 3 in a strain of E. coli.

* * * * *